(12) United States Patent
Sullivan et al.

(10) Patent No.: US 6,861,055 B2
(45) Date of Patent: Mar. 1, 2005

(54) HUMAN GDP-MANNOSE 4,6-DEHYDRATASE

(75) Inventors: Francis Sullivan, Belmont, MA (US);
Ronald Kriz, Hudson, MA (US);
Ravindra Kumar, Belmont, MA (US)

(73) Assignee: Genetics Institute, LLC, Cambridge, MA (US)

( * ) Notice: Subject to any disclaimer, the term of this patent is extended or adjusted under 35 U.S.C. 154(b) by 108 days.

(21) Appl. No.: 09/878,574

(22) Filed: Jun. 11, 2001

(65) Prior Publication Data

US 2003/0235572 A9 Dec. 25, 2003

Related U.S. Application Data

(60) Continuation of application No. 09/333,177, filed on Jun. 14, 1999, now abandoned, which is a division of application No. 09/149,674, filed on Sep. 9, 1998, now Pat. No. 5,942,228, which is a division of application No. 08/984,246, filed on Dec. 3, 1997, now Pat. No. 5,869,307, which is a division of application No. 08/753,233, filed on Nov. 22, 1996, now Pat. No. 5,728,568.

(51) Int. Cl.$^7$ ............................................. A61K 39/395
(52) U.S. Cl. ............................... 424/130.1; 530/387.9; 530/388.1; 530/389.1; 435/190; 424/141.1
(58) Field of Search ................................. 435/190, 189, 435/4, 25; 530/387.9, 388.1, 389.1, 350; 424/130.1, 141.1, 94.4

(56) References Cited

FOREIGN PATENT DOCUMENTS

WO      WO 95/30001      11/1995      ........... C12N/15/12

OTHER PUBLICATIONS

Broschat et al., "Purification and Characterization of GDP–D–mannose 4,6–dehydratase from Porcine Thyroid", *Eur. J. Biochem.* 153:397–401 (1985).
Fujiwara et al., Database DDBT, Accession No. D61843 (1995).
Genbank Accession No. U17055 (1996).
Genbank Accession No. U32570 (1996).
Genbank Accession No. U42580 (1996).
Kaufman, R., "Selection and Coamplification of Heterologous Genes in Mammalian Cells", *Meth. Enzym.* 185:537–566 (1990).
Kaufman et al., "Improved Vectors for Stable Expression of Foreign Genes in Mammalian Cells by Use of the Untranslated Leader Sequence from EMC Virus", *Nuc. Acid Res.*, 19:4485–4490 (1991).
Kornfled et al., "Control of Synthesis of Guanosine 5'–diphosphate D–mannose and Guanosine 5'–diphosphate L–fucose in Bacteria", *Biochem. Biophys. Acta* 117:79–87 (1966).
Li et al., "Analysis of 43Kb of the Chlorella Virus PBCV–1330–Kb Genome Map Positions 45 to 88", *Virol.*, 212:134–150 (1995).
Yamamoto et al., "Evidence that the Enzyme Catalyzing the Conversion of Guanosine Diphosphate D–mannose to a 4–keto Sugar Nucleotide Intermediate Requires Nicotinamide Adenine Dinucleotide Phosphate", *Arch. Biochem. Biophys.* 300:694–698 (1993).

*Primary Examiner*—P. Achutamurthy
*Assistant Examiner*—Yong D. Pak
(74) *Attorney, Agent, or Firm*—Finnegan, Henderson, Farabow, Garrett & Dunner, L.L.P.

(57) ABSTRACT

The invention provides a novel GDP-mannose 4,6-dehydratase.

37 Claims, No Drawings

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 1521 base pairs (B) TYPE: nucleic acid
                (C) STRANDEDNESS: double
                (D) TOPOLOGY: linear (ii) MOLECULE TYPE: cDNA (xi) SEQUENCE DESCRIPTION: SEQ ID NO: 1:

| | | | | | |
|---|---|---|---|---|---|
| GCCGCGTTCC | TGCCGGCACC | GCGCCTGCCC | TCTGCCGCGC | TCCGCCCTGC | CGCCGACCGC | 60 |
| ACGCCCGCCG | CGGGACATGG | CACACGCACC | GGCACGCTGC | CCCAGCGCCC | GGGGCTCCGG | 120 |
| GGACGGCGAG | ATGGGCAAGC | CCAGGAACGT | GGCGCTCATC | ACCGGTATCA | CAGGCCAGGA | 180 |
| TGGTTCCTAC | CTGGCTGAGT | TCCTGCTGGA | GAAAGGCTAT | GAGGTCCATG | GAATTGTACG | 240 |
| GCGGTCCAGT | TCATTTAATA | CGGGTCGAAT | TGAGCATCTG | TATAAGAATC | CCCAGGCTCA | 300 |
| CATTGAAGGA | AACATGAAGT | TGCACTATGG | CGATCTCACT | GACAGTACCT | GCCTTGTGAA | 360 |
| GATCATTAAT | GAAGTAAAGC | CCACAGAGAT | CTACAACCTT | GGAGCCCAGA | GCCACGTCAA | 420 |
| AATTTCCTTT | GACCTCGCTG | AGTACACTGC | GGACGTTGAC | GGAGTTGGCA | CTCTACGACT | 480 |
| TCTAGATGCA | GTTAAGACTT | GTGGCCTTAT | CAACTCTGTG | AAGTTCTACC | AAGCCTCAAC | 540 |
| AAGTGAACTT | TATGGGAAAG | TGCAGGAAAT | ACCCCAGAAG | GAGACCACCC | CTTTCTATCC | 600 |
| CCGGTCACCC | TATGGGGCAG | CAAAACTCTA | TGCCTATTGG | ATTGTGGTGA | ACTTCCGTGA | 660 |
| GGCGTATAAT | CTCTTTGCAG | TGAACGGCAT | TCTCTTCAAT | CATGAGAGTC | CCAGAAGAGG | 720 |
| AGCTAATTTC | GTTACTCGAA | AAATTAGCCG | GTCAGTAGCT | AAGATTTACC | TTGGACAACT | 780 |
| GGAATGTTTC | AGTTTGGGAA | ATCTGGATGC | CAAACGAGAT | TGGGGCCATG | CCAAGGACTA | 840 |
| TGTGGAGGCT | ATGTGGTTGA | TGTTGCAGAA | TGATGAGCCG | GAGGACTTCG | TTATAGCTAC | 900 |
| TGGGGAGGTC | CATAGTGTCC | GGGAATTTGT | CGAGAAATCA | TTCTTGCACA | TTGGAAAAAC | 960 |
| CATTGTGTGG | GAAGGAAAGA | ATGAAAATGA | AGTGGGCAGA | TGTAAAGAGA | CCGGCAAAGT | 1020 |
| TCACGTGACT | GTGGATCTCA | AGTACTACCG | GCCAACTGAA | GTGGACTTTC | TGCAGGGCGA | 1080 |
| CTGCACCAAA | GCGAAACAGA | AGCTGAACTG | GAAGCCCCGG | GTCGCTTTCG | ATGAGCTGGT | 1140 |
| GAGGGAGATG | GTGCACGCCG | ACGTGGAGCT | CATGAGGACA | AACCCCAATG | CCTGAGCAGC | 1200 |
| GCCTCGGAGC | CCGGCCCGCC | CTCCGGCTAC | AATCCCCGCA | GAGTCTCCGG | TGCAGACGCG | 1260 |
| CTGCGGGGAT | GGGGAGCGGC | GTGCCAATCT | GCGGGTCCCC | TGCGGCCCCT | GCTGCCGCTG | 1320 |
| CGCTGTCCCG | GCCGCAAGAG | CGGGGCCGCC | CCGCCGAGGT | TTGTAGCAGC | CGGGATGTGA | 1380 |
| CCCTCCAGGG | TTTGGGTCGC | TTTGCGTTTG | TCGAAGCCTC | CTCTGAATGG | CTTTGTGAAA | 1440 |
| TCAAGATGTT | TTAATCACAT | TCACTTTACT | TGAAATTATG | TTGTTACACA | ACAAATTGTG | 1500 |
| GGGCCTTCAA | ATTGTTTTTC | | | | | 1521 |

(2) INFORMATION FOR SEQ ID NO: 2:

(i) SEQUENCE CHARACTERISTICS:
            (A) LENGTH: 354 amino acids
            (B) TYPE: amino acid
            (C) STRANDEDNESS: <Unknown>
            (D) TOPOLOGY: linear (ii) MOLECULE TYPE: protein (xi) SEQUENCE DESCRIPTION: SEQ ID NO: 2:

Met Gly Lys Pro Arg Asn Val Ala Leu Ile Thr Gly Ile Thr Gly Gln
1               5                   10                  15

Asp Gly Ser Tyr Leu Ala Glu Phe Leu Leu Glu Lys Gly Tyr Glu Val
                20                  25                  30

-continued

```
His Gly Ile Val Arg Arg Ser Ser Phe Asn Thr Gly Arg Ile Glu
        35                  40                  45

His Leu Tyr Lys Asn Pro Gln Ala His Ile Glu Gly Asn Met Lys Leu
 50                  55                  60

His Tyr Gly Asp Leu Thr Asp Ser Thr Cys Leu Val Lys Ile Ile Asn
65                   70                  75                   80

Glu Val Lys Pro Thr Glu Ile Tyr Asn Leu Gly Ala Gln Ser His Val
                 85                  90                  95

Lys Ile Ser Phe Asp Leu Ala Glu Tyr Thr Ala Asp Val Asp Gly Val
                100                 105                 110

Gly Thr Leu Arg Leu Leu Asp Ala Val Lys Thr Cys Gly Leu Ile Asn
                115                 120                 125

Ser Val Lys Phe Tyr Gln Ala Ser Thr Ser Glu Leu Tyr Gly Lys Val
        130                 135                 140

Gln Glu Ile Pro Gln Lys Glu Thr Thr Pro Phe Tyr Pro Arg Ser Pro
145                 150                 155                 160

Tyr Gly Ala Ala Lys Leu Tyr Ala Tyr Trp Ile Val Val Asn Phe Arg
                165                 170                 175

Glu Ala Tyr Asn Leu Phe Ala Val Asn Gly Ile Leu Phe Asn His Glu
                180                 185                 190

Ser Pro Arg Arg Gly Ala Asn Phe Val Thr Arg Lys Ile Ser Arg Ser
        195                 200                 205

Val Ala Lys Ile Tyr Leu Gly Gln Leu Glu Cys Phe Ser Leu Gly Asn
210                 215                 220

Leu Asp Ala Lys Arg Asp Trp Gly His Ala Lys Asp Tyr Val Glu Ala
225                 230                 235                 240

Met Trp Leu Met Leu Gln Asn Asp Glu Pro Glu Asp Phe Val Ile Ala
                245                 250                 255

Thr Gly Glu Val His Ser Val Arg Glu Phe Val Glu Lys Ser Phe Leu
                260                 265                 270

His Ile Gly Lys Thr Ile Val Trp Glu Gly Lys Asn Glu Asn Glu Val
        275                 280                 285

Gly Arg Cys Lys Glu Thr Gly Lys Val His Val Thr Val Asp Leu Lys
290                 295                 300

Tyr Tyr Arg Pro Thr Glu Val Asp Phe Leu Gln Gly Asp Cys Thr Lys
305                 310                 315                 320

Ala Lys Gln Lys Leu Asn Trp Lys Pro Arg Val Ala Phe Asp Glu Leu
                325                 330                 335

Val Arg Glu Met Val His Ala Asp Val Glu Leu Met Arg Thr Asn Pro
                340                 345                 350

Asn Ala
```

(2) INFORMATION FOR SEQ ID NO: 3:

(i) SEQUENCE CHARACTERISTICS:
        (A) LENGTH: 372 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 3:

```
Met Ala His Ala Pro Ala Arg Cys Pro Ser Ala Arg Gly Ser Gly Asp
 1               5                  10                  15

Gly Glu Met Gly Lys Pro Arg Asn Val Ala Leu Ile Thr Gly Ile Thr
```

-continued

```
                    20                  25                  30
Gly Gln Asp Gly Ser Tyr Leu Ala Glu Phe Leu Leu Glu Lys Gly Tyr
            35                  40                  45

Glu Val His Gly Ile Val Arg Arg Ser Ser Phe Asn Thr Gly Arg
    50                  55                  60

Ile Glu His Leu Tyr Lys Asn Pro Gln Ala His Ile Glu Gly Asn Met
65                  70                  75                  80

Lys Leu His Tyr Gly Asp Leu Thr Asp Ser Thr Cys Leu Val Lys Ile
                85                  90                  95

Ile Asn Glu Val Lys Pro Thr Glu Ile Tyr Asn Leu Gly Ala Gln Ser
            100                 105                 110

His Val Lys Ile Ser Phe Asp Leu Ala Glu Tyr Thr Ala Asp Val Asp
        115                 120                 125

Gly Val Gly Thr Leu Arg Leu Leu Asp Ala Val Lys Thr Cys Gly Leu
    130                 135                 140

Ile Asn Ser Val Lys Phe Tyr Gln Ala Ser Thr Ser Glu Leu Tyr Gly
145                 150                 155                 160

Lys Val Gln Glu Ile Pro Gln Lys Glu Thr Thr Pro Phe Tyr Pro Arg
                165                 170                 175

Ser Pro Tyr Gly Ala Ala Lys Leu Tyr Ala Tyr Trp Ile Val Val Asn
            180                 185                 190

Phe Arg Glu Ala Tyr Asn Leu Phe Ala Val Asn Gly Ile Leu Phe Asn
        195                 200                 205

His Glu Ser Pro Arg Arg Gly Ala Asn Phe Val Thr Arg Lys Ile Ser
    210                 215                 220

Arg Ser Val Ala Lys Ile Tyr Leu Gly Gln Leu Glu Cys Phe Ser Leu
225                 230                 235                 240

Gly Asn Leu Asp Ala Lys Arg Asp Trp Gly His Ala Lys Asp Tyr Val
                245                 250                 255

Glu Ala Met Trp Leu Met Leu Gln Asn Asp Glu Pro Glu Asp Phe Val
            260                 265                 270

Ile Ala Thr Gly Glu Val His Ser Val Arg Glu Phe Val Glu Lys Ser
        275                 280                 285

Phe Leu His Ile Gly Lys Thr Ile Val Trp Glu Gly Lys Asn Glu Asn
    290                 295                 300

Glu Val Gly Arg Cys Lys Glu Thr Gly Lys Val His Val Thr Val Asp
305                 310                 315                 320

Leu Lys Tyr Tyr Arg Pro Thr Glu Val Asp Phe Leu Gln Gly Asp Cys
                325                 330                 335

Thr Lys Ala Lys Gln Lys Leu Asn Trp Lys Pro Arg Val Ala Phe Asp
            340                 345                 350

Glu Leu Val Arg Glu Met Val His Ala Asp Val Glu Leu Met Arg Thr
        355                 360                 365

Asn Pro Asn Ala
    370
```

(2) INFORMATION FOR SEQ ID NO: 4:

(i) SEQUENCE CHARACTERISTICS:
(A) LENGTH: 30 bases
(B) TYPE: nucleic acid
(C) STRANDEDNESS: single
(D) TOPOLOGY: linear (ii) MOLECULE TYPE: oligoucleotide

```
        (xi) SEQUENCE DESCRIPTION: SEQ ID NO: 4:

TGATGAGCCA GAGGACTTTG TCATAGCTAC                                              30

(2) INFORMATION FOR SEQ ID NO: 5:

(i) SEQUENCE CHARACTERISTICS:
         (A) LENGTH: 30 bases
         (B) TYPE: nucleic acid
         (C) STRANDEDNESS: single
         (D) TOPOLOGY: linear (ii) MOLECULE TYPE: oligoucleotide (xi) SEQUENCE DESCRIPTION: SEQ ID NO: 5:

CAGAAAGTCC ACTTCAGTCG GTCGGTAGTA                                              30
```

HUMAN GDP-MANNOSE 4,6-DEHYDRATASE

This is request for filing a continuation application under 37 CFR 1.53(b), of prior application Ser. No. 09/333,177 filed on Jun. 14, 1999 now abandoned (CPA filed Jun. 19, 2000), of Francis Sullivan, Ronald Kriz, Ravindra Kumar entitled Human GDP-Mannose 4,6 Dehydratase which is a CPA of Ser. No. 09/333,177 filed on Jun. 14, 1999, which in turn is a divisional application of Ser. No. 09/149,674 filed on Sep. 9, 1998, U.S. Pat. No. 5,942,228, which in turn is a divisional application of Ser. No. 08/984,246 filed on Dec. 3, 1997, U.S. Pat. No. 5,869,307, which in turn is a divisional application of Ser. No. 08/753,233 filed on Nov. 22, 1996, U.S. Pat. No. 5,728,568.

The present invention relates to the cloning and isolation of a human GDP-mannose 4,6 dehydratase, which is useful (among other purposes) for the manufacture of complex carbohydrates and as a target for screening of small molecule antagonists of activity of the enzyme.

BACKGROUD OF THE INVENTION

Complex carbohydrate moieties play an important role in many ligand/receptor binding events. For example, P-selectin ligand (see WO95/30001) found on the surface of neutrophils contains sialyl Lewisx(sLe$_x$) moieties which are essential to binding of the ligand to its receptor. P-selectin, on the surface of vascular endothelium. The interaction of P-selectin ligand and P-selectin is involved in the development of inflammatory responses, including both those which produce desired immune responses and those which cause disease states. As a result, many complex carbohydrate moieties, including sLe$_x$ are currently under investigation for use as therapeutics to interfere with detrimental ligand/receptor binding events.

Complex carbohydrates are usually synthesized with the aid of enzymes which can convert more easily obtainable starting materials and intermediates into necessary moieties which are more difficult to produce by non-enzymatic chemical synthesis. For example, sLe$_x$ contains an essential fucose moiety which can be added enzymatically starting with GDP-fucose, which is readily obtained from GDP-mannose using the appropriate enzymes. As a result, the identification and isolation of a wide variety of enzymes for such purpose has been a continuing goal for those interested in carbohydrate production. In particular, the identification of enzymes capable of coverting GDP-mannose to GDP-fucose has been sought to aid in the development of production methods for sLe$_x$ and other fucose-containing carbohydrates.

One route of synthesis which is used in the production of fucose-containing carbohydrates is through the conversion of GDP-mannose to GDP-fucose, which can. then be used to incorporate the fucose moiety into the synthetic product. This conversion involves multiple steps, each of which can be catalyzed by an appropriate enzyme. The first step in this process is the conversion of GDP-mannose to GDP-4-keto-6-deoxy-mannose. In vivo this conversion is made by the action of an GDP-mannose 4,6-dehydratase.

A GDP-mannose dehydratase enzyme has been cloned and isolated from *E.coli* (GenBank accession number U38473). However, the enzymes from different species may have different in vivo and in vitro characteristics and activities, both beneficial and detrimental, which may affect their relative usefulness for production of complex carbohydrates. Nevertheless, no human dehydratase enzyme has yet been identified.

Certain disease states have also been associated with defects in the action of such dehydratases. For example, the human disease leukocyte adhesion deficiency II (LADII) may be due to a defect in the dehydratase enzyme. The correlation of other dehydratase enzymes with disease states will allow the examination of therapies for such conditions.

Since these dehydratase enzymes are also responsible for the in vivo production of fucose-containing carbohydrate moieties, blocking their activity through the use of antagonists or other means can provide another route for interruption of unwanted inflammatory responses and other conditions dependent upon the production of fucose-containing carbohydrate moieties. Isolated dehydratases can be used as a target to screen for inhibitors of enzyme activity which can be used for this purpose.

Therefore, it would be desirable to identify, clone and isolate additional dehydratase enzymes to expand the panoply of enzymes available to the carbohydrate synthetist. It would also be desirable to identify additional dehydratase which are associated with certain disease states to allow the examination and development of treatments for such conditions. It would also be desirable to identify and isolate additional human dehydratase enzymes which can serve as targets for screening inhibitors.

SUMMARY OF THE INVENTION

In certain embodiments, the present invention provides an isolated polynucleotide comprising a nucleotide sequence selected from the group consisting of:
(a) the nucleotide sequence of SEQ ID NO: 1;
(b) a nucleotide sequence encoding the amino acid sequence of SEQ ID NO:2;
(c) a nucleotide sequence encoding the amino acid sequence of SEQ ID NO:3;
(d) a nucleotide sequence encoding a fragment of the amino acid sequence of (b) or (c) having GM4,6D activity;
(e) a nucleotide sequence capable of hybridizing with the sequence of (a) which encodes a peptide having GM4, 6D activity; and
(f) allelic variants of the sequence of (a), (b) or (c).

Preferably, the nucleotide sequence comprises the nucleotide sequence of SEQ ID NO:1, a nucleotide sequence encoding the amino acid sequence of SEQ ID NO:2, or a nucleotide sequence encoding the amino acid sequence of SEQ ID NO:3. Expression vectors comprising such polynucleotide and an expression control sequence and host cells transformed with such vectors are also provided.

Other embodiments provide for a process for producing a GM4,6D, said process comprising:
(a) establishing a culture of the host cell of the present invention in a suitable culture medium; and
(b) isolating said enzyme from said culture (including without limitation from conditioned media, cell lysate or inclusion bodies).

Compositions comprising a peptide made according to such processes are also provided.

Compositions comprising peptides encoded by polynucleotides of the present invention are also provided.

In yet further embodiments, the present invention provides compositions comprising a peptide comprising an amino acid sequence selected from the group consisting of:
(a) the amino acid sequence of SEQ ID NO:2;
(b) the amino acid sequence of SEQ ID NO:3; and
(c) a fragment of the amino acid sequence of (a) or (b) having GM4,6D activity;

said peptide being substantially free from association with other proteins. Preferably, the peptide comprises the amino acid sequence of SEQ ID NO:2 or SEQ ID NO:3. Pharmaceutical compositions comprising such peptides and a pharmaceutcically acceptable carrier are also provided.

Other embodiments of the present invention provide for a method for identifying an inhibitor of GM4,6D activity, said method comprising:

(a) combining a substrate, a candidate inhibitor compound, and a composition comprising a GM4,6D peptide; and (b) observing whether said GM4,6D peptide converts said substrate.

Inhibitors according to such methods and pharmaceutical compositions incorporating them are also provided.

The invention also provides compositions comprising an antibody which binds to the peptide of the present invention.

Methods are also provided for treating or ameliorating diseases affected by the level of cellular fucosylation or diseases affected by the fucosylation of glycoconjugates. Such methods of treatment comprise administering a pharmaceutical composition comprising an inhibitor of GM4,6D activity to a mammalian subject.

DETAILED DESCRIPTION OF THE INVENTION

Applicants have cloned and isolated a novel human GDP-mannose 4,6-dehydratase (hereinafter "GM4,6D").

A cDNA encoding the GM4,6D of the present invention was isolated as described in Example 1. The sequence of the cDNA is reported as SEQ ID NO:1. Two predicted amino acid sequence encoded by such cDNA are reported as SEQ ID NO:2 and SEQ ID NO:3. The invention also encompasses allelic variations of the cDNA sequence as set forth in SEQ ID NO:1, that is, naturally-occurring alternative forms of the cDNA of SEQ ID NO: 1 which also encode enzymes of the present invention.

A cDNA clone ("P-38-1") encoding the GM4,6D enzyme of the invention was deposited with the American Type Culture Collection on Nov. 15, 1996 as accession number ATCC 98260.

The human enzyme GDP-mannose 4,6-dehydratase (GM4,6D) converts GDP-mannose to GDP-4-keto-6-deoxy-mannose as the first step in the conversion of GDP-mannose to GDP-fucose. As used herein, "GM4,6D activity" means the ability to convert GDP-mannose to GDP4-keto-6-deoxy-mannose, including without limitation such activity as measured by the assays described in Example 2 below or similar assays.

The polynucleotides of the present invention could be used to produce protein for the manufacture of GDP-fucose from GDP-mannose and for the identification of inhibitors of the enzyme's activity. GDP-fucose would be useful in the production of fucosylated glycoconjugates such as sialyl lewis X and its derivatives. Inhibitors of the enzyme would be useful in treating human conditions where fucose play a role such as inflammation and inflammatory disorders, arthritis, transplant rejection, asthma, sepsis, reperfusion injury, stroke, infection, reproduction and development.

Polynucleotides encoding GM4,6D would also be useful in developing an assay for defects in the enzyme, such as potentially might occur in Leukocyte deficiency type II, LADII. The polynucleotides could be used in gene replacement therapy. The gene sequence could also be used to modify cell line to increase the amounts of GDP-fucose that they make, for use in production of recombinant proteins.

Also included in the invention are isolated DNAs which hybridize to the DNA sequence set forth in SEQ ID NO:1 under stringent (e.g. 4×SSC at 65° C. or 50% formamide and 4×SSC at 42° C.), or relaxed (4×SSC at 50° C. or 30–40% formamide at 42° C.) conditions.

The isolated polynucleotides of the invention may be operably linked to an expression control sequence such as the pMT2 or pED expression vectors disclosed in Kaufman et al., Nucleic Acids Res. 19, 4485–4490 (1991), in order to produce the GM4,6D peptides recombinantly. Many suitable expression control sequences are known in the art. General methods of expressing recombinant proteins are also known and are exemplified in R. Kaufman, Methods in Enzymology 185, 537–566 (1990). As defined herein "operably linked" means enzymatically or chemically ligated to form a covalent bond between the isolated polynucleotide of the invention and the expression control sequence, in such a way that the GM4,6D peptide is expressed by a host cell which has been transformed (transfected) with the ligated polynucleotide/expression control sequence.

A number of types of cells may act as suitable host cells for expression of the GM4,6D peptide. Suitable host cells are capable of attaching carbohydrate side chains characteristic of functional GM4,6D peptide. Such capability may arise by virtue of the presence of a suitable glycosylating enzyme within the host cell, whether naturally occurring, induced by chemical mutagenesis, or through transfection of the host cell with a suitable expression plasmid containing a polynucleotide encoding the glycosylating enzyme. Host cells include, for example, monkey COS cells. Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, or HaK cells.

The GM4,6D peptide may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin* No. 1555 (1987), incorporated herein by reference.

Alternatively, it may be possible to produce the GM4,6D peptide in lower eukaryotes such as yeast, fungi or in prokaryotes such as bacteria. Potentially suitable yeast strains include *Saccharomyces cerevisiae, Schizosaccharomyces pombe, Kluyveromyces* strains, *Candida,* or any yeast strain capable of expressing heterologous proteins. Potentially suitable bacterial strains include *Escherichia coli, Bacillus subtilis, Salmonella typhimurium*, or any bacterial strain capable of expressing heterologous proteins. Suitable fungi strains include *Aspergillus* sp. or any fungi strain capable of expressing heterologous proteins.

The GM4,6D peptide of the invention may also be expressed as a product of transgenic animals. e.g., as a component of the milk of transgenic cows, goats, pigs, or sheep which are characterized by somatic or germ cells containing a polynucleotide encoding the GM4,6D peptide.

The GM4,6D peptide of the invention may be prepared by culturing transformed host cells under culture conditions necessary to express a GM4,6D peptide of the present invention. The resulting expressed protein may then be purified from culture medium or cell extracts as described in the examples below.

Alternatively, the GM4,6D peptide of the invention is concentrated using a commercially available protein concentration filter, for example, an Amicon or Millipore Pellicon ultrafiltration unit Following the concentration step, the concentrate can be applied to a purification matrix such as a gel filtration medium.

Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred (e.g., S-Sepharose® columns). The purification of the GM4,6D peptide from culture supernatant may also include one or more column steps over such affinity resins as concanavalin A-agarose, heparin-toyopearl® or Cibacrom blue 3GA Sepharose®; or by hydrophobic interaction chromatography using such resins as phenyl ether, butyl ether, or propyl ether; or by immunoaffinity chromatography.

Finally, one or more reverse-phase high performance liquid chromatography (RP-HPLC) steps employing hydrophobic RP-HPLC media, e.g., silica gel having pendant methyl or other aliphatic groups, can be employed to further purify the GM4,6D peptide. Some or all of the foregoing purification steps, in various combinations, can also be employed to provide a substantially homogeneous isolated recombinant protein. The GM4,6D peptide thus purified is substantially free of other mammalian or other host cell proteins and is defined in accordance with the present invention as "isolated GM4,6D peptide".

The GM4,6D of the present invention may be used to screen unknown compounds having inhibitory activity for the dehydratase and, by derivation, inhibitory activity for conditions affected by overexpression or other undesirable level of activity of such enzyme. Many assays for dehydratase activity are known and may be used with enzyme of the present invention to screen unknown compounds. For example, such assays include those described in Example 2. These assays may be performed manually or may be automated or robotized for faster screening. Methods of automation and robotization are known to those skilled in the art.

In one possible screening assay, a first mixture is formed by combining a GM4,6D peptide of the present invention with GDP-mannose by such peptide, and the amount of conversion in the first mixture ($B_0$) is measured. A second mixture is also formed by combining the peptide, the substrate and the compound or agent to be screened, and the amount of conversion in the second mixture (B) is measured. The amounts of conversion in the first and second mixtures are compared, for example, by performing a $B/B_o$ calculation. A compound or agent is considered to be capable of inhibiting enzyme activity if a decrease in conversion in the second mixture as compared to the first mixture is observed. The formulation and optimization of mixtures is within the level of skill in the art, such mixtures may also contain buffers and salts necessary to enhance or to optimize the assay, and additional control assays may be included in the screening assay of the invention.

Other uses for the GM4,6D of the present invention are in the development of monoclonal and polyclonal antibodies. Such antibodies may be generated by employing purified forms of the enzyme or immunogenic fragments thereof as an antigen using standard methods for the development of polyclonal and monoclonal antibodies as are known to those skilled in the art. Such polyclonal or monoclonal antibodies are useful as research or diagnostic tools, and further may be used to study enzyme activity and disease states related to such enzyme.

Pharmaceutical compositions containing inhibitors (e.g., anti-inflammatory agents) identified by the screening method of the present invention may be employed to treat, for example, diseases affected by the level of cellular fucosylation or the fucosylation of glycoconjugates including, protein, lipids and glycosaminoglycans. Pharmaceutical compositions of the invention comprise a therapeutically effective amount of such an inhibitor compound first identified according to the present invention in a mixture with an optional pharmaceutically acceptable carrier. The term "pharmaceutically acceptable" means a non-toxic material that does not interfere with the effectiveness of the biological activity of the active ingredient(s). The term "therapeutically effective amount" means the total amount of each active component of the method or composition that is sufficient to show a meaningful patient benefit, i.e., healing or amelioration of chronic conditions or increase in rate of healing or amelioration. When applied to an individual active ingredient, administered alone, the term refers to that ingredient alone. When applied to a combination, the term refers to combined amounts of the active ingredients that result in the therapeutic effect, whether administered in combination, serially or simultaneously. A therapeutically effective dose of the inhibitor of this invention is contemplated to be in the range of about 0.1 µg to about 100 mg per kg body weight per application. It is contemplated that the duration of each application of the inhibitor will be in the range of 12 to 24 hours of continuous administration. The characteristics of the carrier or other material will depend on the route of administration.

The amount of inhibitor in the pharmaceutical composition of the present invention will depend upon the nature and severity of the condition being treated, and on the nature of prior treatments which the patient has undergone. Ultimately, the attending physician will decide the amount of inhibitor with which to treat each individual patient. Initially, the attending physician will administer low doses of inhibitor and observe the patient's response. Larger doses of inhibitor may be administered until the optimal therapeutic effect is obtained for the patient, and at that point the dosage is not increased further.

Administration may be intravenous, but other known methods of administration for inhibitory and anti-inflammatory agents may be used. Administration of the inhibitory compounds identified by the method of the invention can be carried out in a variety of conventional ways. For example, for topical administration, the inhibitor compound of the invention will be in the form of a pyrogen-free, dermatologically acceptable liquid or semi-solid formulation such as an ointment, cream, lotion, foam or gel. The preparation of such topically applied formulations is within the skill in the art. Gel formulation should contain, in addition to the inhibitor compound, about 2 to about 5% W/W of a gelling agent The gelling agent may also function to stabilize the active ingredient and preferably should be water soluble. The formulation should also contain about 2% W/V of a bactericidal agent and a buffering agent. Exemplary gels include ethyl, methyl, and propyl celluloses. Preferred gels include carboxypolymethylene such as Carbopol (934P; B.F. Goodrich), hydroxypropyl methylcellulose phthalates such as Methocel (K100M premium. Merril Dow), cellulose gums such as Blanose (7HF; Aqualon, U.K.), xanthan gums such as Keltrol (TF; Kelko International), hydroxyethyl cellulose oxides such as Polyox (WSR 303; Union Carbide), propylene glycols, polyethylene glycols and mixtures thereof. If Carbopol is used, a neutralizing agent, such as NaOH, is also required in order to maintain pH in the desired range of about 7 to about 8 and most desirably at about 7.5. Exemplary preferred bactericidal agents include steryl alcohols, especially benzyl alcohol. The buffering agent can be any of those already known in the art as useful in preparing medicinal formulations, for example 20 mM phosphate buffer, pH 7.5.

Cutaneous or subcutaneous injection may also be employed and in that case the inhibitor compound of the invention will be in the form of pyrogen-free, parenterally acceptable aqueous solutions. The preparation of such parenterally acceptable solutions, having due regard to pH, isotonicity, stability, and the like, is within the skill in the art.

Intravenous injection may be employed, wherein the inhibitor compound of the invention will be in the form of pyrogen-free, parenterally acceptable aqueous solutions. A preferred pharmaceutical composition for intravenous injection should contain, in addition to the inhibitor compound, an isotonic vehicle such as Sodium Chloride Injection, Ringer's Injection, Dextrose Injection, Dextrose and Sodium Chloride Injection. Lactated Ringer's Injection, or other vehicle as known in the art The pharmaceutical composition according to the present invention may also contain stabilizers, preservatives, buffers, antioxidants, or other additive known to those of skill in the art.

The amount of inhibitor compound in the pharmaceutical composition of the present invention will depend upon the nature and severity of the condition being treated, and on the nature of prior treatments which the patient has undergone. Ultimately, the attending physician will decide the amount of inhibitor compound with which to treat each individual patient.

Inhibitor compounds identified using the method of the present invention may be administered alone or in combination with other anti-inflammation agents and therapies.

EXAMPLE 1

Cloning of cDNA for GM4,6D

HL-60 cDNA Library Construction

A cDNA library was constructed from HL-60 cells as described in U.S. patent WO95/30001. This is a plasmid based cDNA library, constructed as 38 separate pools each, representing 3,.000 to 50,000 individual clones.

Clone Identification

The 38 library pools were combined in pairs to produce a total of 19 pools. 100 ng of DNA was taken from each pool and used as template for a polymerase chain reaction using the following two GDP mannose dehydratase deoxyribonucleotides:

5'-TGATGAGCCAGAGGACTTTGTCATAGCTAC-3' (SEQ ID NO:4)

5'-CAGAAAGTCCACTTCAGTCGGTCGGTAGTA-3' (SEQ ID NO:5)

The reaction conditions were set up as recommended by the manufacturer of Taq polymerase (Perkin Elmer) and the cycle conditions were as follows: 94°1 min, 68° 3 min. Repeat for 30 cycles.

At the end of the reaction, an aliquot is taken and examined by agarose gel to determine the pools containing the dehydratase gene. The reaction done on combined pools (29 and 30) as well as (37 and 38) gave the expected 200 bp fragment. These pools were then examined separately and the positive pools were determined to be pool #30 and #38. The 200 bp PCR product was agarose gel purified and an aliquot was used for a subsequent reamplification and purification to further purify the fragment away from nonspecific products. This purified fragment was then random primer labeled with $^{32}P$ following standard protocols, and was used as probe to identify GDP-MD clones. A total of ~150,000 colonies from each pool were plated on $LB_{amp100}$, the colonies were transferred to nitrocellulose and hybridized to probe using stringent hybridization conditions. Positive colonies were subjected to one round of colony purification, and individual positive clones were purified and confirmed by DNA sequence determination.

EXAMPLE 2

Enzyme Activity Assays

Assays of dehydratase include, without limitation, incubation of radiolabeled ($^{14}C$ or $^{3}H$) on unlabeled GDP-mannose in the presence of salts, buffers and cofactors with enzyme or enzyme extracts, and separation of the reactants and products by HPLC (for example, as described in Yamamoto et al. (1993) Archives of Biochemistry and Biophysics, vol. 300, 694–698). Alternatively, dehydratase activity can be assayed by coupling the reaction with the enzyme(s) GDP-4-keto-6-deoxy-mannose, epimerase, reductae and monitoring the coupled oxidation of NADPH using, for example, visible or fluorescent spectroscopy (for example, as described in Yamamoto et al., supra). In another alternative, dehydratase activity can be monitored by following the absorbance of the product GDP4-keto-6-deoxy-mannose at 325 nm in alkali solution (for example, as described by Komfied and Ginsberg (1966) Biochinica et Biophysica Acta, vol. 117, 79–87).

What is claimed is:

1. A method for treating a subject having an inflammatory disorder, wherein the inflammatory disorder is characterized by excessive GDP-mannose 4,6 dehydratase (GM4,6D) activity or excessive GM4,6D nucleic acid expression, comprising administering a therapeutically effective amount of an antibody capable of binding to a polypeptide comprising the amino acid sequence of either SEQ ID NO:2 or SEQ ID NO: 3.

2. The method of claim 1, wherein the antibody is a monoclonal antibody.

3. The method of claim 1, wherein the antibody is a polyclonal antibody.

4. The method of claim 1, wherein the antibody is capable of binding to a polypeptide comprising the amino acid sequence of SEQ ID NO: 3.

5. A method for treating a subject having an inflammatory disorder characterized by excessive GM4,6D activity or excessive GM4,6D nucleic acid expression and chosen frown arthritis, transplant rejection, asthma, sepsis, reperfusion injury, stroke and infection, comprising administering a therapeutically effective amount of an antibody capable of binding to a polypeptide comprising the amino acid sequence of either SEQ ID NO:2 or SEQ ID NO: 3.

6. The method of claim 5, wherein the antibody is a monoclonal antibody.

7. The method of claim 5, wherein the antibody is a polyclonal antibody.

8. The method of claim 5, wherein the inflammatory disorder is arthritis.

9. The method of claim 5, wherein the inflammatory disorder is transplant rejection.

10. The method of claim 5, wherein the inflammatory disorder is asthma.

11. The method of claim 5, wherein the inflammatory disorder is stroke.

12. The method of claim 5, wherein the inflammatory disorder is infection.

13. A method of treating a subject having an inflammatory disorder characterized by excessive GM4,6D polypeptide activity comprising administering to the subject a compound, wherein said compound modulates GM4,6D polypeptide activity when combined with a substrate and a GM4,6D polypeptide chosen from:

(1) a polypeptide encoded by the nucleotide sequence of SEQ ID NO: 1;

(2) a polypeptide of SEQ ID NO: 2;

(3) a polypeptide of SEQ ID NO: 3;

(4) and a fragment of the polypeptide of SEQ ID NO:2 or SEQ ID NO: 3, which has GM4,6D activity.

14. The method of claim 13, wherein the compound is an antibody that binds the GM4,6D polypeptide.

15. The method of claim 13, wherein the antibody is a monoclonal antibody.

16. The method of claim 13, wherein the antibody is a polyclonal antibody.

17. The method of claim 1, wherein the antibody is capable of binding a polypeptide comprising the amino acid sequence of SEQ ID NO:2.

18. The method of claim 1, wherein the antibody is capable of binding a polypeptide consisting of the amino acid sequence of SEQ ID NO:2.

19. The method of claim 1, wherein the antibody is capable of binding a polypeptide consisting of the amino acid sequence of SEQ ID NO:3.

20. The method of claim 5, wherein the antibody is capable of binding a polypeptide comprising the amino acid sequence of SEQ ID NO:2.

21. The method of claim 5, wherein the antibody is capable of binding a polypeptide comprising the amino acid sequence of SEQ ID NO:3.

22. The method of claim 5, wherein the antibody is capable of binding a polypeptide consisting of the amino acid sequence of SEQ ID NO:2.

23. The method of claim 5, wherein the antibody is capable of binding a polypeptide consisting of the amino acid sequence of SEQ ID NO:3.

24. The method of claim 5, wherein the inflammatory disorder is sepsis.

25. The method of claim 5, wherein the inflammatory disorder is reperfusion injury.

26. The method of claim 14, wherein the antibody is capable of binding a polypeptide comprising the amino acid sequence of SEQ ID NO:2.

27. The method of claim 14, wherein the antibody is capable of binding a polypeptide comprising the amino acid sequence of SEQ ID NO:3.

28. The method of claim 14, wherein the antibody is capable of binding a polypeptide consisting of the amino acid sequence of SEQ ID NO:2.

29. The method of claim 14, wherein the antibody is capable of binding a polypeptide consisting of the amino acid sequence of SEQ ID NO:3.

30. The method of claim 13, wherein the inflammatory disorder is chosen from arthritis, transplant rejection, asthma, sepsis, reperfusion injury, stroke and infection.

31. The method of 30, wherein the inflammatory disorder is arthritis.

32. The method of claim 30, wherein the inflammatory disorder is transplant rejection.

33. The method of claim 30, wherein the inflammatory disorder is asthma.

34. The method of claim 30, wherein the inflammatory disorder is sepsis.

35. The method of claim 30, wherein the inflammatory disorder is reperfusion injury.

36. The method of claim 30, wherein the inflammatory disorder is stroke.

37. The method of claim 30, wherein the inflammatory disorder is infection.

* * * * *

UNITED STATES PATENT AND TRADEMARK OFFICE
CERTIFICATE OF CORRECTION

PATENT NO. : 6,861,055 B2
DATED : March 1, 2005
INVENTOR(S) : Sullivan et al.

It is certified that error appears in the above-identified patent and that said Letters Patent is hereby corrected as shown below:

Column 15,
Line 39, change "frown" to -- from --.

Column 17,
Line 1, change "of 30," to -- of claim 30, --.

Signed and Sealed this

Sixth Day of September, 2005

JON W. DUDAS
*Director of the United States Patent and Trademark Office*